US012789185B2

(12) United States Patent
Sando et al.

(10) Patent No.: US 12,789,185 B2
(45) Date of Patent: Nov. 10, 2026

(54) CARTRIDGE WITH MIXING ZONE FOR ENDOTOXIN DETECTION

(71) Applicant: LONZA WALKERSVILLE, INC., Walkersville, MD (US)

(72) Inventors: Gerald Sando, Walkersville, MD (US); Candice Stumbaugh, Walkersville, MD (US); Adrian Grandison, Walkersville, MD (US); Leben Tadesse, Walkersville, MD (US); Puja Sawhney, Walkersville, MD (US); Will Harris, Walkersville, MD (US); Rupert Barton, Walkersville, MD (US)

(73) Assignee: Lonza Walkersville, Inc., Walkersville, MD (US)

(*) Notice: Subject to any disclaimer, the term of this patent is extended or adjusted under 35 U.S.C. 154(b) by 981 days.

(21) Appl. No.: 17/634,612

(22) PCT Filed: Aug. 13, 2020

(86) PCT No.: PCT/US2020/046049

§ 371 (c)(1),
(2) Date: Feb. 11, 2022

(87) PCT Pub. No.: WO2021/034581

PCT Pub. Date: Feb. 25, 2021

(65) Prior Publication Data

US 2022/0323952 A1 Oct. 13, 2022

Related U.S. Application Data

(60) Provisional application No. 62/889,747, filed on Aug. 21, 2019.

(51) Int. Cl.
*B01L 3/00* (2006.01)
*G01N 33/579* (2006.01)

(52) U.S. Cl.
CPC ........ *B01L 3/50273* (2013.01); *G01N 33/579* (2013.01); *B01L 2300/0816* (2013.01); *B01L 2400/084* (2013.01)

(58) Field of Classification Search
None
See application file for complete search history.

(56) References Cited

U.S. PATENT DOCUMENTS 4,188,264 A 2/1980 Iwanaga et al.
4,510,241 A 4/1985 Mills
(Continued)

FOREIGN PATENT DOCUMENTS

JP 2007-501020 A 1/2007
JP 2012-132879 A 7/2012
JP 2012-215535 A 11/2012

OTHER PUBLICATIONS

International Search Report and Written Opinion issued in PCT/US2020/046049, mailed Jan. 13, 2021.
(Continued)

*Primary Examiner* — Henry H Nguyen
(74) *Attorney, Agent, or Firm* — Medler Ferro Woodhouse & Mills PLLC

(57) ABSTRACT

The present invention is directed to methods, compositions and devices useful for the detection and/or quantification of a microbial contaminant, including an endotoxin. In embodiments, cartridges are provided that suitably include dried compositions that are useful in absorbance-based assays and in combination with portable readers/devices.

6 Claims, 9 Drawing Sheets

(56) References Cited

U.S. PATENT DOCUMENTS

| | | | | |
|---|---|---|---|---|
| 5,310,657 | A | 5/1994 | Berzofsky | |
| 5,605,806 | A | 2/1997 | Tanaka et al. | |
| 5,731,212 | A * | 3/1998 | Gavin | G01N 33/4905 436/514 |
| 10,352,934 | B2 | 7/2019 | Godec | |
| 2004/0241788 | A1 | 12/2004 | Wainwright et al. | |
| 2005/0255600 | A1 | 11/2005 | Padmanabhan et al. | |
| 2006/0013725 | A1* | 1/2006 | Larsen | G01N 15/12 422/400 |
| 2009/0266421 | A1* | 10/2009 | Linder | B01L 3/502746 137/1 |
| 2010/0047851 | A1 | 2/2010 | Wainwright et al. | |
| 2010/0112723 | A1* | 5/2010 | Battrell | G01N 33/53 422/68.1 |
| 2011/0034348 | A1* | 2/2011 | Deutsch | C12M 23/12 506/14 |
| 2012/0088263 | A1* | 4/2012 | Bruno | B01L 3/5025 435/287.1 |
| 2013/0171663 | A1 | 7/2013 | Kuroda et al. | |
| 2015/0130463 | A1 | 5/2015 | Wellman et al. | |
| 2015/0293097 | A1 | 10/2015 | Godec | |
| 2018/0038864 | A1 | 2/2018 | Stumbaugh et al. | |
| 2018/0208964 | A1 | 7/2018 | Stumbaugh et al. | |
| 2019/0001330 | A1 | 1/2019 | Sando et al. | |
| 2019/0201905 | A1* | 7/2019 | Bianchessi | B01L 3/502715 |
| 2020/0254454 | A1* | 8/2020 | Spero | B01L 3/502746 |

OTHER PUBLICATIONS

Klein, "Laser Welding of Plastics, " Wiley-VCH, Germany (2012).

Shoh, "Welding of thermoplastics by ultrasound," Ultrasonics 14: 209-217 (1976).

* cited by examiner

CARTRIDGE WITH MIXING ZONE FOR ENDOTOXIN DETECTION

BACKGROUND OF THE INVENTION

Field of the Invention

The present invention is directed to methods, compositions and devices useful for the detection and/or quantification of a microbial contaminant, including an endotoxin. In embodiments, cartridges are provided that suitably include dried compositions that are useful in absorbance-based assays and in combination with portable readers/devices.

Background of the Invention

Microbial contamination, including contamination from Gram positive bacteria, Gram negative bacteria, yeast, fungi, and molds, can cause severe illness and, in some cases, even death in humans. The pharmaceutical, medical device, and food industries often require frequent, accurate, and sensitive testing for the presence of such microbial contaminants to meet certain standards, for example, standards imposed by the United States Food and Drug Administration (USFDA) or Environmental Protection Agency.

What is needed is a convenient and rapid way to analyze samples for the presence of microbial contaminants, suitably with a compact, portable device that can be easily used in a variety of situations. The present invention meets these needs.

BRIEF SUMMARY OF THE INVENTION

In embodiments, provided herein is a cartridge for determining the presence and/or amount of a microbial contaminant in a sample, the cartridge comprising a housing including an optical sample well, a fluid inlet port and a conduit fluidly connecting the fluid inlet port and the optical sample well; a pump mechanism associated with the housing and fluidly connected to the fluid inlet port, the conduit and the optical sample well; a mixing zone located along the conduit configured to include a dried composition including a hemocyte lysate.

In further embodiments, provided herein is a cartridge for determining the presence and/or amount of a microbial contaminant in a sample, the cartridge comprising: a housing including a cover section, a base section mechanically connected to the cover section, and a manifold section mechanically connected to the base section; the base section including two optical sample wells, a fluid inlet port and a conduit fluidly connecting the fluid inlet port and the optical sample well; the conduit including an aspiration zone, a fluid restrictor, and a mixing zone; the manifold section including a mixing portion configured to include a dried composition comprising a hemocyte lysate, the mixing portion corresponding to the mixing zone of the conduit; and a pump mechanism associated with the housing and fluidly connected to the fluid inlet port, the conduit and the two optical sample wells.

Also provided herein is a method for detecting the presence of a microbial contaminant in a sample, the method comprising: introducing the sample into the fluid inlet port of a cartridge described herein, and transferring the sample to the conduit; transferring the sample into the mixing zone of the conduit; mixing the sample with the hemocyte lysate and the chromogenic substrate to generate a mixed sample; transferring the mixed sample from the mixing zone to the sample well; and measuring an optical property of the mixed sample in the optical sample well, wherein a change in the optical property is indicative of the presence of the microbial contaminant in the sample.

In further embodiments, provided herein is a method for detecting the presence of a microbial contaminant in a sample, the method comprising: introducing the sample into the fluid inlet port of a cartridge described herein, and transferring the sample to the aspiration zone; transferring the sample from the aspiration zone, through the fluid restrictor, to the mixing zone; mixing the sample with the hemocyte lysate and the chromogenic substrate to generate a mixed sample; transferring the mixed sample to the optical sample wells; and measuring an optical property of the mixed sample in the optical sample wells, wherein a change in the optical property is indicative of the presence of the microbial contaminant in the sample.

Further embodiments, features, and advantages of the embodiments, as well as the structure and operation of the various embodiments, are described in detail below with reference to accompanying drawings.

BRIEF DESCRIPTION OF THE DRAWINGS/FIGURES

DETAILED DESCRIPTION OF THE INVENTION

Figure 1A:
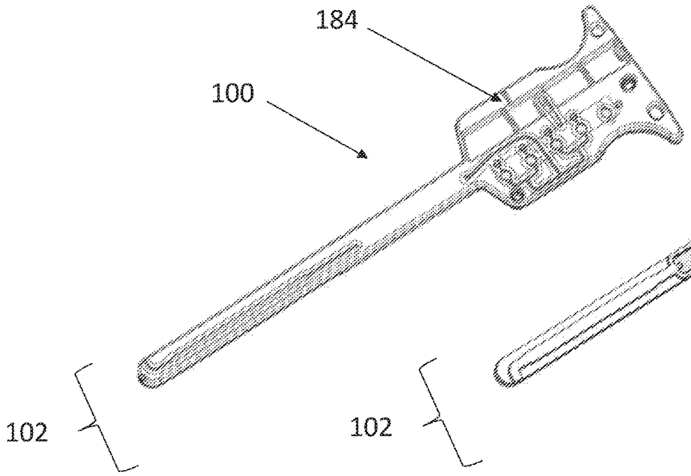
FIGS. 1A-1G show various views and components of cartridges for endotoxin detection in accordance with embodiments hereof.

It should be appreciated that the particular implementations shown and described herein are examples and are not intended to otherwise limit the scope of the application in any way.

The published patents, patent applications, websites, company names, and scientific literature referred to herein are hereby incorporated by reference in their entireties to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined. Reference is made herein to various methodologies and materials known to those of ordinary skill in the art.

Testing for Microbial Contaminants

A variety of assays have been developed to detect the presence and/or amount of a microbial contaminant in a test sample. Hemocyte lysates prepared from the hemolymph of crustaceans, for example, horseshoe crabs, are often utilized. These assays typically exploit, in one way or another, a clotting cascade that occurs when the hemocyte lysate is exposed to a microbial contaminant. Examples of hemocyte lysates include the amoebocyte lysate (AL) produced from the hemolymph of a horseshoe crab, *Limulus polyphemus, Tachypleus gigas, Tachypleus tridentatus*, and *Carcinoscorpius rotundicauda*. Amoebocyte lysates produced from the hemolymph of *Limulus, Tachypleus*, and *Carcinoscorpius* species are referred to as Limulus amoebocyte lysate (LAL), *Tachypleus amoebocyte* lysate (TAL), and *Carcinoscorpius amoebocyte* lysate (CAL), respectively.

Assays that use LAL include, for example, gel clot assays, end point turbidimetric assays, kinetic turbidimetric assays, and endpoint chromogenic assays (Prior (1990) "Clinical Applications of the Limulus Amoebocyte Lysate Test" CRC PRESS 28-34). These assays, however, suffer from one or more disadvantages including reagent expense, assay speed and limited sensitivity ranges. Also, these assays typically require that samples be sent to a testing facility removed from the origin of the sample being tested.

Cartridge for Endotoxin Detection

In embodiments, provided herein is a cartridge for determining the presence and/or amount of a microbial contaminant in a sample. Samples that can be tested using the various cartridges, devices and methods described herein include liquid samples, such as from biological processes, or pharmaceutical formulations, and can be large scale or small scale processes.

As shown in FIG. 1A, in embodiments, cartridge 100, includes housing 102, which provides the structural support for the cartridge. As used herein "cartridge" means a self-contained element for receiving and holding a sample that is to be tested for the presence and/or amount of a microbial contaminant.

Housing 102 can be prepared from any suitable material including various plastics or glasses. Housing 102 can be prepared from a single piece of material, or as described herein, can include separate pieces or sections joined together to create the housing 102 and thus the overall cartridge 100.

Housing 102 includes optical sample well 104. FIG. 1F shows a side view of optical sample well 104, which is in the form of a vessel or ampule between the upper and lower surfaces of housing 102. Optical sample well 104 is suitably constructed from a plastic or glass material, and suitably is optically clear or transparent, so as to allow light to pass through the bottom and top of the optical sample well, thereby allowing the light to contact a sample contained within the optical sample well. In embodiments, optical sample well 104, as well as the remainder of housing 102, can be prepared from a yellow colored glass or polymer, which suitably blocks light of about 400 nm to about 450 nm from passing (i.e., 405 nm), but allows other wavelengths to pass. Such embodiments reduce the amount light passing through optical sample well 104, reducing cross-talk and increasing the sensitivity of the methods described herein by reducing stray light. Optical well 104 is suitably in the shape a cylinder having an outer wall, and upper and lower surfaces as the the top and bottom of the well, suitably formed from various elements of housing 102.

Housing 102 of cartridge 100 also further includes fluid inlet port 106 and conduit 108. Fluid inlet port 106 is suitably a tube, slit, hole or other suitable opening at the end of a long or slender section 119 of housing 102, inside of which conduit 108 is housed, wherein the fluid inlet port is used for contacting a sample. Fluid inlet port 106 is designed so as to allow a sample to be drawn upward, in sample introduction direction 114 (FIG. 1F), into the fluid inlet port. Conduit 108 fluidly connects fluid inlet port 106 and optical sample well 104. That is, conduit 108 provides a tubular or microfluidic connection between tip of fluid inlet port 106 and optical sample well 104, that allows for transfer of a liquid sample between the fluid inlet port, after being drawn into the port, through conduit 108, and into optical sample well 104. In embodiments, conduit 108 can be formed as channels cut into the surface of housing 102, or can be formed as tubing or microtubing from various polymers such as poly(styrene), etc.

In embodiments, conduit 108 suitably includes a first section that can be used to retain a fluid sample following introduction into fluid inlet 106. As shown in FIGS. 1F and 1G, upon introduction of a sample into fluid inlet port 106 in sample introduction direction 114, the sample travels to an aspiration zone 140, i.e., an initial position within conduit 108, where the sample is held and maintained prior to transferring further into conduit 108. Suitably, aspiration zone 140 has a volume of about 0.05 μL to about 500 μL, and is used as an initial volume holder for a sample following introduction into the cartridge. This aspiration zone 140 can be engaged by the user of the cartridge, when the cartridge is inserted into a test sample, and the desired volume is initially drawn into the sample inlet port 106, for later testing. In exemplary embodiments, the volume of aspiration zone 140 is about 10 μL to about 200 μL, more suitably about 30 μL to about 100 μL, about 30 μL to about 80 μL, about 30 μL to about 50 μL, or about 30 μL, about 40 μL, or about 50 μL.

Cartridge 100 suitably further includes a mixing zone 142 located along conduit 108. Mixing zone 142 is suitably separated from sample inlet port 106 and aspiration zone 140 (if included) by a fluid restrictor 144. Mixing zone 142 is configured to include (and in exemplary embodiments suitably includes) a dried composition including a hemocyte lysate. As described herein, mixing zone provides a portion of conduit 108 where a sample thought to contain a microbial contaminant, is introduced so that the sample can be mixed with a dried composition including a hemocyte lysate. As described herein, mixing zone 142 also further includes a chromogenic substrate. Thus, the mixing zone 142 provides an area where a test sample can be contacted with both a hemocyte lysate and the chromogenic substrate, suitably both dried (either dried as separate components or dried together in the same dried composition), and then the sample mixed with the hemocyte lysate and the chromogenic substrate. Various mechanisms can be used to mix the liquid test sample and the hemocyte lysate and a chromogenic substrate, and can include for example, a magnetic stirring element 146 (see FIG. 1G), such as a stir bar, stir rod, or small magnetic bead or sphere. For example, when cartridge 100 is placed in a reader or other suitable mechanism, a magnet can be placed beneath, above, or around, mixing zone 142, and the magnetic stirring element 146 rotated, translated, or otherwise moved within the mixing zone to agitate and move the test sample and mix the sample with the components that have been dried (or otherwise added) to the mixing zone. Other mixing mechanisms can include various agitators, either internal or external, including tapping mechanisms, agitating or shaking mechanisms, ultrasound mechanisms, etc. In exemplary embodiments, the volume of mixing zone 142 is about 10 μL to about 200 μL, more suitably about 30 μL to about 100 μL, about 30 μL to about 80 μL, about 30 μL to about 50 μL, or about 30 μL, about 40 μL, or about 50 μL.

In exemplary embodiments, a fluid restrictor 144 is located between aspiration zone 140 and mixing zone 142, and can be any suitable mechanism or structure that reduces flow between sample inlet port 106/aspiration zone 140, and the further downstream mixing zone 142. In embodiments, fluid restrictor 144 is a piece or element of plastic placed within conduit 108, or can be a part of conduit 108, or in other embodiments can simply be a narrowing of conduit 108, that acts as a way to slow fluid entering sample inlet port 106, from traveling further down conduit 108, and instead allowing a fluid sample to collect in aspiration zone 140. In embodiments, fluid restrictor 144 acts as a dam between the aspiration zone and the mixing zone. In embodiments, fluid restrictor 144 is not a valve, in that it cannot be turned on or off, but rather provides a mechanism to slow fluid movement to allow for proper filling of the various components along the conduit. In further embodiments, however, a valve structure can be added to conduit 108 to control fluid flow between any of the various components along the length of the conduit.

In embodiments, cartridge 100 further includes a pump mechanism 110 associated with housing 102. Pump mechanism 110 suitably is a three-position syringe (one-position, two-position, four-position, five-position, etc., syringes can also be used), which includes a barrel 118 (see FIGS. 1G and 3A) and plunger 116, which can slide within the barrel. Pump mechanism 110 can be attached directly to housing 102 via a suitable mechanism (e.g., glue, adhesive, mechanical bands, wraps or staples, etc.) or can be an element prepared as an integrated part of housing 102 (for example as part of base section 186 of the housing). Pump mechanism 110 is fluidly connected to fluid inlet port 106, conduit 108, and optical sample well 104, such that upon actuation of pump mechanism 110, a sample can be drawn into fluid inlet port 106, and then into conduit 108, for example as shown in FIG. 1F, with 114 illustrating the sample introduction direction, and then further into sample well 104, as described herein.

In exemplary embodiments, pump mechanism 110, suitably a three-position syringe, moves into a first position which causes the sample to transfer into fluid inlet port 106 and conduit 108, and suitably into aspiration zone 140, but not to pass through, over or around fluid restrictor 144. For example, a vacuum can be generated by a three-position syringe to introduce or draw the sample into fluid inlet port 106, and then into conduit 108 and aspiration zone 140. Pump mechanism 110 suitably moves to a second position, which provides transport of the sample from aspiration zone 140, through fluid restrictor 144, and into mixing zone 142. Following mixing of the sample with the various dried components, pump mechanism 100 suitably moves to a third position, where the mixed sample is now transported to optical sample well 104 (again through another section of conduit 108).

Introducing or drawing a sample into fluid inlet port 106, and then conduit 108, and suitably maintaining the sample in aspiration zone 140 with pump mechanism 110 at a first position, allows cartridge 100 with the sample to be prepared at a location of sampling (e.g., an assembly line, plant, facility, sample vats or storage tanks), and then maintained in a state of readiness, prior to detection or measurement. An advantage of this design is that the sample can be held in cartridge 100 for a period of time (suitably minutes (e.g., 10-30 minutes) up to about 1-2 hours, or longer) prior to making a measurement of the sample, thus allowing for multiple different samples to be taken without the fear of loss of sample quality. In addition, if further activities are required following the taking of a sample, these can be carried out, and then the sample analyzed at a later time.

In embodiments, the length of conduit 108, which can include the length from the tip of fluid inlet port 106, to the sample well 104, is on the order of about 1 cm to about 15 cm, more suitably about 1 cm to about 10 cm, or about 1 cm to about 5 cm. Conduit 108 can include aspiration zone 140 and mixing zone 142 (as well as other zones or sections if desired) that are on the order of about 0.2 mm to about 10 mm in length, with the full length of the conduit 108 being on the order of about 5 mm to about 50 mm. The diameter or cross-sectional width of conduit 108 is suitably on the order of about 0.1 mm to about 1 mm, about 0.5 mm to about 1 mm, about 0.5 mm to about 0.8 mm, or about 0.1 mm, about 0.2 mm, about 0.3, about 0.4 mm, about 0.5 mm, about 0.6 mm, about 0.7 mm or about 0.8 mm. Use of a cross-sectional width of conduit 108 on the order of about 0.5 mm helps in reducing wicking and preventing sample loss. In embodiments, fluid restrictor 144 suitably allows for fluid to pass over or through the restrictor through a diameter of about 0.05 mm to about 1 mm. In embodiments, conduit 108 can include a bent or doubled-over pattern (or other similar orientation that maximizes length of conduit 108 while minimizing surface area), and in other embodiments, conduit 108 can be a substantially straight channel from the tip of the fluid inlet port to the sample well. In other embodiments, more than one conduit can be present, such as 2, 3, 4, 5, 6, 7, 8, 9, or 10 or more conduits. The use of sections of conduit 108 having lengths on the order of about 0.2 mm to about 1 mm helps in reducing wicking, air pocket formation and loss of sample, while the sample is being readied for analysis, including in the devices/readers described herein.

Sample sizes that can be maintained within conduit 108, prior to measurement and analysis are suitably on the order of about 25 μl to about 200 μl, more suitably about 50 μl to about 150 μl, about 50 μl to about 100 μl, about 50 μl to about 80 μl, or about 40 μl, about 50 μl, about 60 μl, about 65 μl, about 70 μl, about 75 μl, about 80 μl, about 90 μl, or about 100 μl. In embodiments, the entire volume that can be contained within cartridge 100 is suitably about 50 μl to about 150 μl, about 50 μl to about 100 μl, about 50 μl to about 80 μl, or about 40 μl, about 50 μl, about 60 μl, about 65 μl, about 70 μl, about 75 μl, about 80 μl, about 90 μl, or about 100 μl.

In embodiments, housing 102 suitably includes four optical sample wells 104, wherein two of the four optical sample wells are configured to include (and suitably include) an agent representative of the microbial contaminant dried in the optical sample wells. In other embodiments, housing 102 can include two optical sample wells 104, where one of the two optical sample wells is configured to include (and suitably includes) an agent representative of the microbial contaminant dried in the optical sample well.

The size of optical sample well 104, and thus suitably the volume that can be maintained with the well, is dictated by the height of the well wall, and the diameter of the top and bottom of the well. Suitably, optical sample well 104 will have a height on the order of about 100 μm to about 20 mm, more suitably about 100 μm to about 10 mm or about 100 μm to about 5 mm, and a diameter on the order of about 100 μm to about 20 mm, more suitably about 100 μm to about 10 mm or about 100 μm to about 5 mm. In embodiments, optical sample well 104 suitably holds about 1 μL to about 5 mL of sample, or about 1 μL to about 1 mL or about 1 μL to about 500 μL, about 1 μL to about 50 μL, about 1 μL to about 20 μL, about 1 μL to about 10 μL, or about 1 μl, about 2 μl, about 3 μl, about 4 μl, about 5 μl, about 6 μl, about 7 μl, about 8 μl, about 9 μl, about 10 μl, about 11 μl, about 12 μl, about 13 μl, about 14 μl, or about 15 μl.

As described herein, suitably the mixing zone 142 includes a dried composition, which includes a hemocyte lysate. As used herein "dried composition" includes substances that are freeze-dried, lyophilized or vitrified, to form a dried cake, powder, crystal or film. Methods of lyophilization or vitrification are known in the art. The dried composition is suitably dried onto the mixing zone 142 (i.e., on the sides of the zone), or can be provided as dried onto manifold section 188 as described herein, or can be in the form of a free pellet that is included with/in mixing zone or can be added to mixing zone as desired/required.

As used herein, the term, "hemocyte lysate" means any lysate, or a fraction or component thereof, produced by the lysis and/or membrane permeabilization of hemocytes, for example, amoebocytes and hemolymph cells, (i) extracted from a crustacean or insect and/or (ii) cultured in vitro after extraction from the host. Hemocyte cellular material that has been extruded from hemolymph cells by contact with a membrane permeabilization agent such as a $Ca^{2+}$ ionophore or the like (i.e., extruded other than by lysis) or otherwise extracted without cellular lysis is also considered to be a hemocyte lysate.

An exemplary hemocyte lysate is an amoebocyte lysate prepared from the blood of a crustacean, for example, a horseshoe crab or Jonah crab. As used herein, the term "amoebocyte lysate" is understood to mean any lysate or fraction or component thereof produced by the lysis, extrusion, or extraction of the cellular contents from amoebocytes extracted from a crustacean, for example, a horseshoe crab. The amoebocyte lysate comprises at least one component of an enzymatic cascade and/or produces a clot in the presence of an endotoxin, for example, a Gram negative bacterial endotoxin and/or a glucan, for example, a (1→3)-β-D glucan, produced by a yeast or a mold. Exemplary amoebocyte lysates can be derived from horseshoe crabs, which include crabs belonging to the *Limulus* genus, for example, *Limulus polyphemus*, the *Tachypleus* genus, for example, *Tachypleus gigas*, and *Tachypleus tridentatus*, and the *Carcinoscorpius* genus, for example, *Carcinoscorpius rotundicauda.*

*Limulus* amoebocyte lysate (LAL) is employed as the amoebocyte lysate of choice in many bacterial endotoxin assays because of its sensitivity, specificity, and relative ease for avoiding interference by other components that may be present in a sample. LAL, when combined with a sample containing a bacterial endotoxin and optionally with certain LAL substrates, reacts with the endotoxin in the sample to produce a detectable product, such as a gel, an increase in turbidity, or a colored or light-emitting product, in the case of a synthetic chromogenic substrate. The product may be detected, for example, either visually or by the use of an optical detector.

When bacterial endotoxin is contacted with LAL, the endotoxin initiates a series of enzymatic reactions, referred to in the art as the Factor C pathway, that can involve three serine protease zymogens called Factor C, Factor B, and pro-clotting enzyme. Upon exposure to endotoxin, the endotoxin-sensitive factor, Factor C, is activated. Activated Factor C thereafter hydrolyses and activates Factor B, whereupon activated Factor B activates proclotting enzyme to produce a clotting enzyme. The clotting enzyme thereafter hydrolyzes specific sites, for example, $Arg_{18}$-$Thr_{19}$ and $Arg_{46}$-$Gly_{47}$ of coagulogen, an invertebrate, fibrinogen-like clottable protein, to produce a coagulin gel. See, for example, U.S. Pat. No. 5,605,806.

Methods for enhancing the sensitivity of a hemocyte lysate for endotoxin, for example, include, without limitation, aging the crude hemocyte lysate, adjusting pH, adjusting the concentration of divalent cations, adjusting the concentration of coagulogen, chloroform extraction, and the addition of serum albumin, biocompatible buffers and/or biological detergents.

For example, in embodiments the hemocyte lysate for use in the dried compositions described herein can be a hemocyte lysate that is substantially free of coagulogen. In another embodiment, the hemocyte lysate that is substantially free of coagulogen is LAL substantially free of coagulogen. One of skill in the art, upon reading the present disclosure, would appreciate that a reduction in various amounts of coagulogen will result in increasing levels of speed, sensitivity and/or separation in a chromogenic assay, e.g., an LAL assay. In some embodiments, the term "substantially free" refers to hemocyte lysate having less than 50%, less than 40%, less than 30%, less than 20%, less than 10%, less than 5%, less than 2%, less than 1% or less than 0.5% (wt/wt) of coagulogen relative to total protein in the hemocyte lysate as measured by SDS-PAGE with protein stain and confirmed by Western blot. In some embodiments, the term "substantially free" refers to LAL having less than 50%, less than 40%, less than 30%, less than 20%, less than 10%, less than 5%, less than 2%, less than 1% or less than 0.5% (wt/wt) of coagulogen relative to total protein in the LAL as measured by SDS-PAGE with protein stain and confirmed by Western blot. In some embodiments, the term "substantially free" refers to clarified LAL having less than 50%, less than 40%, less than 30%, less than 20%, less than 10%, less than 5%, less than 2%, less than 1% or less than 0.5% (wt/wt) of coagulogen relative to total protein in the LAL as measured by SDS-PAGE with protein stain and confirmed by Western blot.

In some embodiments, the term "substantially free" refers to hemocyte lysate having less than 10% or less than 5% (wt/wt) of coagulogen relative to total protein in the hemocyte lysate as measured by SDS-PAGE with protein stain and confirmed by Western blot. In some embodiments, the term "substantially free" refers to LAL having less than 10% or less than 5% (wt/wt) of coagulogen relative to total protein in the LAL as measured by SDS-PAGE with protein stain and confirmed by Western blot. In some embodiments, the term "substantially free" refers to clarified LAL having less than 10% or less than 5% (wt/wt) of coagulogen relative to total protein in the LAL as measured by SDS-PAGE with protein stain and confirmed by Western blot.

In some embodiments, the term "substantially free" refers to hemocyte lysate having a concentration of coagulogen at less than about 20 μg/μL, less than about 15 μg/μL, less than about 10 µg/µL, less than about 5 µg/µL, less than about 4 µg/µL, less than about 3 µg/µL, less than about 2 µg/µL, or less than about 1 µg/µL. In some embodiments, the term "substantially free" refers to LAL having a concentration of coagulogen at less than about 20 µg/µL, less than about 15 µg/µL, less than about 10 µg/µL, less than about 5 µg/µL, less than about 4 µg/µL, less than about 3 µg/µL, less than about 2 µg/µL, or less than about 1 µg/µL. In some embodiments, the term "substantially free" refers to clarified LAL having a concentration of coagulogen at less than about 20 µg/µL, less than about 15 µg/µL, less than about 10 µg/µL, less than about 5 µg/µL, less than about 4 µg/µL, less than about 3 µg/µL, less than about 2 µg/µL, or less than about 1 µg/µL.

Exemplary LAL substantially free of coagulogen is described in U.S. Published Patent Application No. 2018/0208964 and 2018/0038864, the disclosures of both which are incorporated by reference herein in their entireties.

One of skill in the art can appreciate that different methods may be used to remove the coagulogen from the hemocyte lystate, e.g., LAL. Each of these methods, may differ in efficiency, rate of purification, cost, and effort, but are within the knowledge of the skilled artisan. In some embodiments, the hemocyte lystate, e.g., LAL, is substantially free of coagulogen, wherein the composition is made by a method comprising: (a) obtaining a solution derived from lysed amebocytes from *Limulus polyphemus*; (b) combining the solution from (a) with a buffer; (c) subjecting the combination from (b) to continuous tangential flow filtration (TFF) using a 20 kDa to 50 kDa membrane filter to produce a retentate; and (d) centrifuging the retentate from (c) at greater than 20,000×g for greater than 25 minutes to produce a supernatant, wherein the supernatant is clarified LAL that is substantially free of coagulogen.

In some embodiments, the hemocyte lysate is a clarified limulus amebocyte lysate. The term "clarified limulus amebocyte lysate" (or "clarified LAL") that is substantially free of coagulogen refers to LAL substantially free of coagulogen, discussed above, that has been further treated to remove components that create a cloudy appearance of the LAL. In embodiments, clarified LAL is created by centrifuging LAL substantially free of coagulogen. In some embodiments, the term "clarified LAL" refers to LAL that has been centrifuged at greater than 1800 g (i.e., 1800×gravity), greater than 2200 g, greater than 2600 g, greater than 3000 g, greater than 3400 g, greater than 3800 g, greater than 4200 g, greater than 4600 g, greater than 5000 g, greater than 5400 g, greater than 5800 g, greater than 6000 g, greater than 6100 g, or greater than 6200 g for a period of time sufficient visibly clear the LAL without damaging the enzymes. In some embodiments, the term "clarified LAL" refers to LAL that has been centrifuged at 1800 to 8000 g, 2200 g to 7600 g, 2600 g to 7200 g, 3000 g to 7200 g, 3400 g to 7200 g, 3800 g to 7200 g, 4200 g to 7200 g, 4600 g to 7200 g, 5000 g to 7200 g, 5400 g to 7200 g, 5800 g to 7200 g, or 6100 g to 7200 g for a period of time sufficient visibly clear the LAL without damaging the enzymes.

In some embodiments, the term "clarified limulus amebocyte lysate" (or "clarified LAL") that is substantially free of coagulogen refers to LAL substantially free of coagulogen, discussed above, that has been further treated to remove components that create a cloudy appearance of the LAL by the centrifuging LAL substantially free of coagulogen at greater than 20,000×g, greater than 22,000×g, greater than 24,000×g, greater than 25,000×g, greater than 26,000×g, greater than 28,000×g, greater than 30,000×g, greater than 35,000×g, greater than 40,000×g, greater than 45,000×g or greater than 50,000×g. In some embodiments, the LAL substantially free of coagulogen is centrifuged a at greater than 20,000-50,000×g, 20,000-40,000×g, 25,000-50,000×g, 25,000-40,000×g, or 30,000-40,000×g. In some embodiments, the LAL substantially free of coagulogen is centrifuged for greater than 20 minutes, greater than 30 minutes, greater than 40 minutes or greater than 60 minutes. In some embodiments, the LAL substantially free of coagulogen is centrifuged for 20-120 minutes, 20-90 minutes, 20-60 minutes, 20-40 minutes or about 30 minutes.

In some embodiments, the term "clarified LAL" refers to LAL that has been centrifuged for greater than 3 minutes, greater than 4 minutes, greater than 5 minutes, greater than 6 minutes, greater than 7 minutes, greater than 8 minutes, greater than 9 minutes, or greater than 10 minutes. In some embodiments, the term "clarified LAL" refers to LAL that has been centrifuged for 3 minute to 30 minutes, 4 minutes to 25 minutes, 4 minutes to 20 minutes, 5 minutes to 15 minutes or 5 minutes to 10 minutes. One of skill in the art can appreciate that a lower speed of centrifugation may require a longer centrifugation time, and will adjust the time and/or speed accordingly to reduce the visual cloudiness of the LAL. In some embodiments, the term "clarified LAL" refers to LAL substantially free of coagulogen centrifuged at about 5000 g to about 7000 g for about 3 minutes to about 10 minutes, or about 6120 g for 5 minutes. In embodiments, clarified LAL substantially free of coagulogen is made by centrifuging a solution derived from lysed amebocytes from *Limulus polyphemus* at 2,000 rpm (980 g) for 8 minutes at 4° C. The clarified LAL is found in the supernatant after centrifugation. In some embodiments the resulting supernatant is then combined with a buffer; the resulting combination of supernatant and buffer is then subjected to tangential flow filtration using a 30 kDa membrane filter to produce a retentate; and the retentate is centrifuged at 5,000 rpm (6120 g) for 5 minutes at 4° C. to produce a supernatant, wherein the supernatant is clarified LAL that is substantially free of coagulogen. In embodiments, the solution derived from lysed amebocytes from *Limulus polyphemus* is a pool of multiple *Limulus polyphemus* lysed amebocytes.

In some embodiments, the hemocyte lysate is obtained by obtaining a solution derived from lysed amebocytes from *Limulus polyphemus*. In some embodiments, the solution is then combined with a buffer; the resulting combination of solution and buffer is then subjected to continuous tangential flow filtration (TFF) using a 20 kDa to 50 kDa membrane filter to produce a retentate; and the retentate is centrifuged at greater than 20,000×g for greater than 25 minutes at 4° C. to produce a supernatant, wherein the supernatant is clarified LAL that is substantially free of coagulogen. In embodiments, the lysate is derived from lysed amebocytes from *Limulus polyphemus* or a pool of multiple *Limulus polyphemus* lysed amebocytes. In some embodiments, the continuous TFF comprises at least four diafiltration volumes (DV). In some embodiments, the continuous TFF comprises at least five diafiltration volumes. In some embodiments, the continuous TFF comprises at least six diafiltration volumes. In some embodiments, the continuous TFF comprises at least 7, at least 8, at least 9, at least 10, at least 11, at least 12, at least 13, at least 14, or at least 15 diafiltration volumes.

Any chromogenic substrate that is cleaved by the clotting enzyme of a hemocyte lysate may be used in the cartridges, methods and compositions described herein. U.S. Pat. No. 5,310,657, for example, describes an exemplary chromogenic substrate having the formula $R_1$-$A_1$-$A_2$-$A_3$-$A_4$-B-$R_2$, where $R_1$ represents hydrogen, a blocking aromatic hydrocarbon or an acyl group; $A_1$ represents an L or D-amino acid selected from Ile, Val or Leu; $A_2$ represents Glu or Asp; $A_3$ represents Ala or Cys; $A_4$ represents Arg; B represents a linkage selected from an ester and an amide; and $R_2$ represents a chromogenic or fluorogenic group which is covalently attached to the C-carboxyl terminal of Arginine through the B linkage, the fluorogenic or chromogenic moiety being capable of being cleaved from the remainder of the chromogenic substrate to produce a chromogen or a fluorogen. An exemplary chromogenic substrate has the consensus sequence acetate-Ile-Glu-Ala-Arg-pNA, where pNA represents a para-nitroaniline group. U.S. Pat. No. 4,188,264 describes a peptide substrate with a structure consisting of L-amino acids in the sequence $R_1$-Gly-Arg-$R_2$ where $R_1$ represents an N-blocked amino acid and $R_2$ is a group that can be released by enzymatic hydrolysis to yield a colored compound, $HR_2$. U.S. Pat. No. 4,510,241 discloses a chromogenic peptide substrate, which differs from the previous substrate in that the Gly moiety is replaced in the sequence by Ala or Cys. Alternatively, the chromogenic substrate may contain a fluorophore, for example, 7-amino-4-methyl coumarin, 7-amino-4-trifluoromethyl coumarin, and 4-methoxy-2-naphthalyamine.

Various concentrations of chromogenic substrates can be used. In some embodiments, the chromogenic substrate has a concentration of 0.1 g/l to 0.5 g/l, 0.1 g/l to 0.4 g/l, 0.2 g/l to 0.4 g/l, 0.2 g/l to 0.3 g/l or 0.2 g/l to 0.25 g/l.

Inhibition or enhancement of the assay occurs when substances in the test sample interfere with the hemocyte lysate reaction. Inhibition results in a longer reaction time, indicating lower levels of microbial contamination than may actually be present in the test sample. Enhancement results in shorter reaction time, indicating higher levels of microbial contamination than may actually be present in the test sample.

Exemplary amounts of hemocyte lysate, chromogenic substrate and/or an agent representative of a microbial contaminant that can dried in the various dried compositions are described herein or otherwise readily determined by those of ordinary skill in the art. In some embodiments, the dried compositions comprise amounts of the components such that a ratio of about 30% to 50% hemocyte lysate, and 10% to 30% chromogenic substrate (v/v), are provided. In some embodiments, the dried compositions comprise amounts of the components such that a ratio of about 35% to about 45% hemocyte lysate and 15% to 25% chromogenic substrate, or about 40% hemocyte lysate, and 20% chromogenic substrate (wt/wt), are provided. In other embodiments, the dried compositions comprise amounts of the components such that a ratio of about 30% to 50% LAL substantially free of coagulogen, and 10% to 30% chromogenic substrate (v/v), are provided. In some embodiments, the dried composition comprises amounts of the components such that a ratio of about 35% to about 45% LAL substantially free of coagulogen and 15% to 25% chromogenic substrate, or about 40% LAL substantially free of coagulogen, and 20% chromogenic substrate (wt/wt), are provided. In other embodiments, the dried compositions comprise amounts of the components such that a ratio of about 30% to 50% clarified LAL, and 10% to 30% chromogenic substrate (v/v), are provided. In some embodiments, the dried composition comprise amounts of the components such that a ratio of about 35% to about 45% clarified LAL and 15% to 25% chromogenic substrate, or about 40% clarified LAL, and 20% chromogenic substrate (wt/wt), are provided.

In some embodiments, the dried compositions comprise about 1 μg to about 50 μg hemocyte lysate, and about 0.1 μg to 5 μg chromogenic substrate, about 1 μg to about 30 μg hemocyte lysate, and about 0.5 μg to 4.0 μg chromogenic substrate, or about 2 μg to about 20 μg hemocyte lysate, and about 1.0 μg to about 3.0 μg chromogenic substrate, or about 4 μg to about 25 μg hemocyte lysate, and about 1.0 μg to about 2 μg chromogenic substrate. In some embodiments, the dried compositions comprises about 1 μg to about 50 μg LAL substantially free of coagulogen and about 0.1 μg to about 5 μg chromogenic substrate, or about 1 μg to about 30 μg LAL substantially free of coagulogen and about 0.5 μg to about 5 μg chromogenic substrate, or about 2 μg to about 20 μg LAL substantially free of coagulogen and about 1.0 μg to about 3.0 μg chromogenic substrate, or about 1 μg to about 30 μg LAL substantially free of coagulogen, and about 1.0 μg to about 2.0 μg chromogenic substrate, wherein the chromogenic substrate is Ac-Ile-Glu-Ala-Arg-pNA. In some embodiments, the dried compositions comprises about 4 μg to about 25 μg LAL substantially free of coagulogen, and about 1 μg to about 1.5 μg chromogenic substrate, wherein the chromogenic substrate is Ac-Ile-Glu-Ala-Arg-pNA. In some embodiments, the dried compositions comprises about 1 μg to about 50 μg clarified LAL and about 0.1 μg to about 5 μg chromogenic substrate, or about 1 μg to about 30 μg clarified LAL and about 0.5 μg to about 5 μg chromogenic substrate, or about 2 μg to about 20 μg clarified LAL and about 1.0 μg to about 3.0 μg chromogenic substrate, or about 1 μg to about 30 μg clarified LAL , and about 1.0 μg to about 2.0 μg chromogenic substrate, wherein the chromogenic substrate is Ac-Ile-Glu-Ala-Arg-pNA. In some embodiments, the dried compositions comprises about 4 μg to about 25 μg clarified LAL, and about 1 μg to about 1.5 μg chromogenic substrate, wherein the chromogenic substrate is Ac-Ile-Glu-Ala-Arg-pNA.

In some embodiments, the microbial contaminant control is about 0.1 EU/ml to 1 EU/ml. In some embodiments, the microbial contaminant is a bacterial endotoxin in a concentration of about 0.1 EU/ml to 1 EU/ml, wherein 1 μl to 10 μl is used.

In suitable embodiments, a formulation containing about 10% to about 60% hemocyte lysate or about 20% to about 50% hemocyte lysate or about 30% to about 40% hemocyte lysate, or about 10% to about 60% LAL substantially free of coagulogen or about 20% to about 50% LAL substantially free of coagulogen or about 30% to about 40% LAL substantially free of coagulogen is lyophilized to yield the dried composition. In some embodiments, a formulation containing about 10% to about 60% clarified LAL or about 20% to about 50% clarified LAL or about 30% to about 40% clarified LAL lyophilized. The volume of the hemocyte lysate, LAL substantially free of coagulogen formulation, or clarified LAL formulation that is lyophilized will generally be on the order of about 1 μL to about 10 μL. In further embodiments, the formulation can contain about 20% to about 30%, or about 25% to about 30% hemocyte lysate or LAL substantially free of coagulogen, with a deposited volume of about 3 μL to about 10 μL, or about 3 μL to about 8 μL, or about 3.5 μL to about 7 μL. In further embodiments, the formulation can contain about 20% to about 30%, or about 25% to about 30% clarified LAL, with a deposited volume of about 3 μL to about 10 μL, or about 3 μL to about 8 μL, or about 3.5 μL to about 7 μL.

Cartridge 100 can also include pH indicator, such as pH paper or other suitable compound or composition which can be used to directly determine the pH of the sample. A pH indicator can be directly associated with optical sample well 104, but can also be associated with conduit 108, depending on the orientation of cartridge 100. In either embodiment, a pH indicator can be readily used to measure sample pH.

Cartridge 100 can also include a bar code, useful for identifying the cartridge for ease in storage and automated data collection, etc.

Figure 1B:
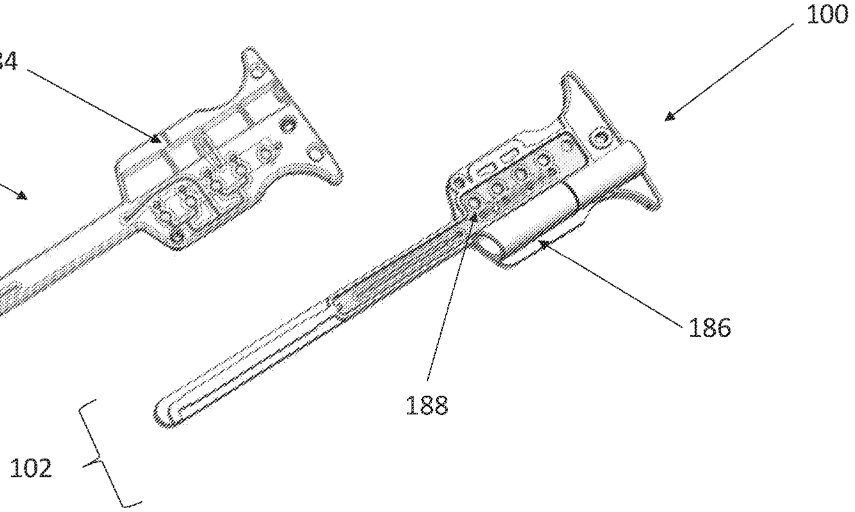

In additional embodiments, for example as shown in FIGS. 1A-1B, housing 102 includes four optical sample wells, though other or additional numbers of optical sample wells, e.g., 2, 3, 4, 5, 6, 7, 8, 9, 10, etc., can be utilized. As described herein, in embodiments, two of the four optical sample wells further include an agent representative of the microbial contaminant dried on the optical sample wells, which can act as a control to verify that the methods described herein are functioning correctly, as are the various substrates, lysates, etc. In other embodiments, housing 102 can include 2 optical sample wells, where one sample well acts as a control and the other a test well, or can include 4, 6, 8, 10, 12, 14, etc., where some portion of the optical sample wells (e.g., 2, 4, 6, 8, etc.) functioning as controls, with the other optical sample wells, function as test wells.

To verify the lack of inhibition or enhancement, control optical sample wells are suitably "spiked" with a known amount of an agent representative of the microbial contaminant to be measured. Suitably, the microbial contaminant spike results in a final microbial contaminant concentration in the sample near to the mid-point, on a log basis, between the microbial contaminant concentration of the highest and lowest standards in a standard curve. For example, in an assay with a standard curve spanning from 50 Endotoxin Units (EU)/mL to 0.005 EU/mL, samples can be spiked to contain a final microbial contaminant concentration of about 0.5 EU/mL. In an assay with a standard curve spanning from 1 EU/mL to 0.01 EU/mL, the microbial contaminant spike can result in a final microbial contaminant concentration of about 0.1 EU/mL.

Suitably, the "spike," or known amount of an agent representative of the microbial contaminant to be measured, is dried onto the optical sample well. The spiked sample(s) is assayed in parallel with the unspiked, or test sample. The resulting microbial contaminant concentration in the unspiked sample and the microbial contaminant recovered in the spiked sample then are calculated and compared. The microbial contaminant recovered suitably equals the known concentration of the spike within about 50-200%. If the sample (or dilution) is found to inhibit or enhance the reaction, the sample may require further dilution until the inhibition or enhancement is overcome. Initially, it may be desirable to screen for inhibition or enhancement by testing 10-fold dilutions of the sample.

In additional embodiments, the dried composition in the mixing zone 142 can include various other reagents/reactants, such that the cartridges described herein can be used for additional reactions. In such embodiments, the ability to introduce the sample into the mixing zone 142, in which a pre-determined amount of desired reactants (e.g., buffers, enzymes, stabilizers, etc.) are included as lyophilized or vitrified dried compositions, provides a platform for various additional testing opportunities beyond endotoxin detection.

In embodiments, as shown in FIG. 1F, housing 102 includes a sample blocking mechanism, suitably a liquid impermeable membrane 121, which aids with filling and maintaining the sample volume in optical sample wells 104. As used herein "liquid impermeable membrane" refers to a substrate that allows air to pass through the substrate, but is largely impermeable to liquids, and suitably does not allow any liquids to pass through the membrane. Examples of such membranes include various rubbers and polymers, including for example, poly(propylene) membranes, poly(tetrafluoroethylene) (PTFE) membranes, other fluoropolymers, etc. Suitably, liquid impermeable membrane 121 is fluidly connected to optical sample well 104, such that the liquid sample that fills the optical sample well, comes in contact with the liquid impermeable membrane, and stops flowing as it impacts liquid impermeable membrane, and thus maintains the volume(s) of sample in each of the optical sample wells such that they are the same (or within about 1-10% of the same volume), so that each sample can be compared with the other.

Figures 1C, 1D, 1E:
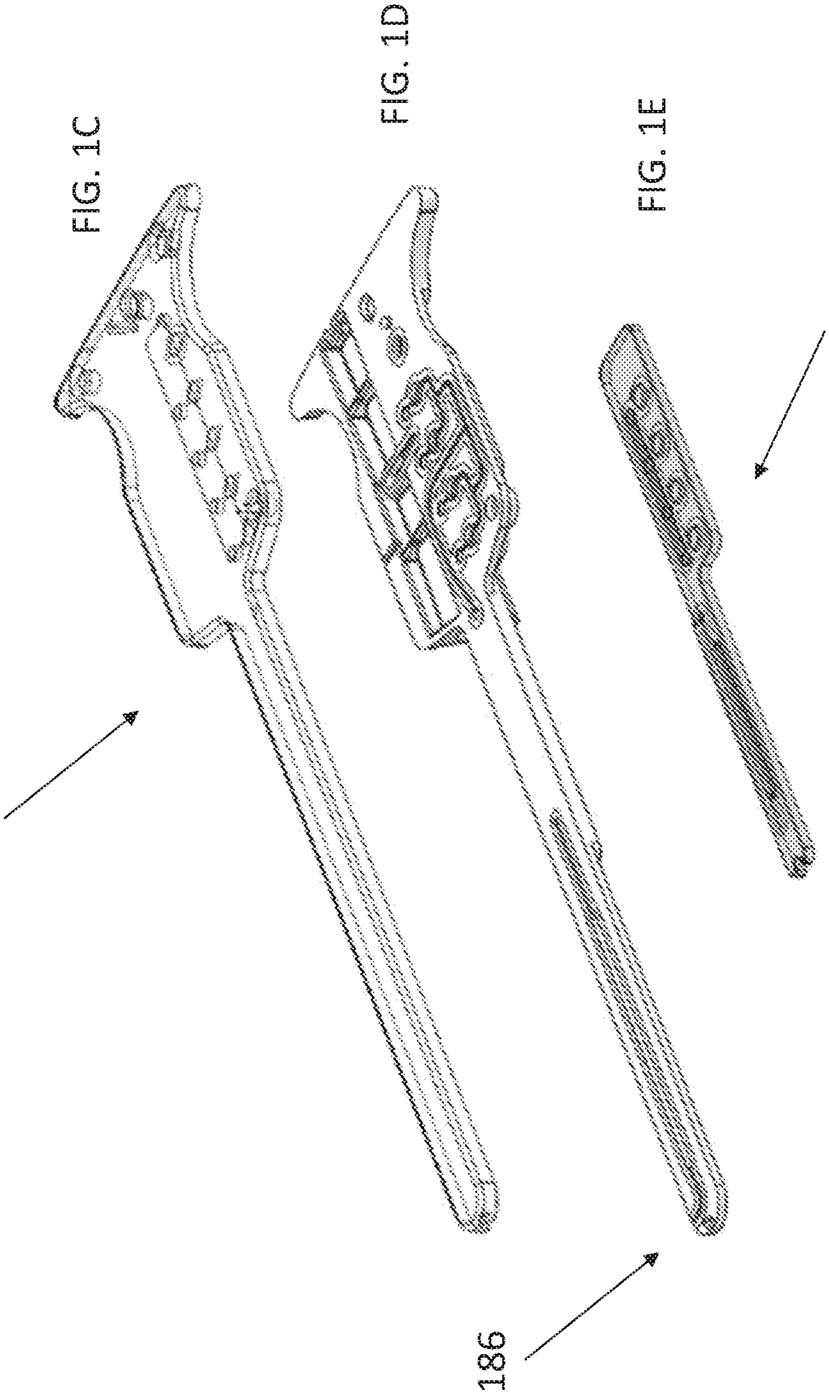
Figure 1F:
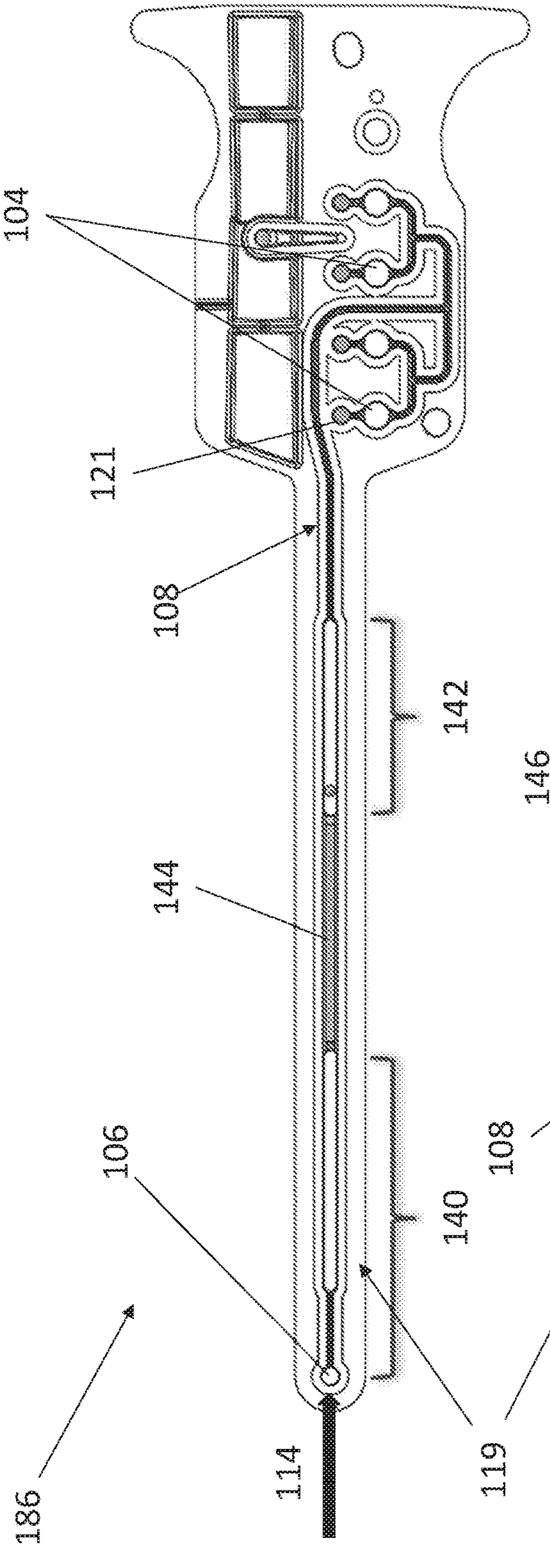
Figure 1G:
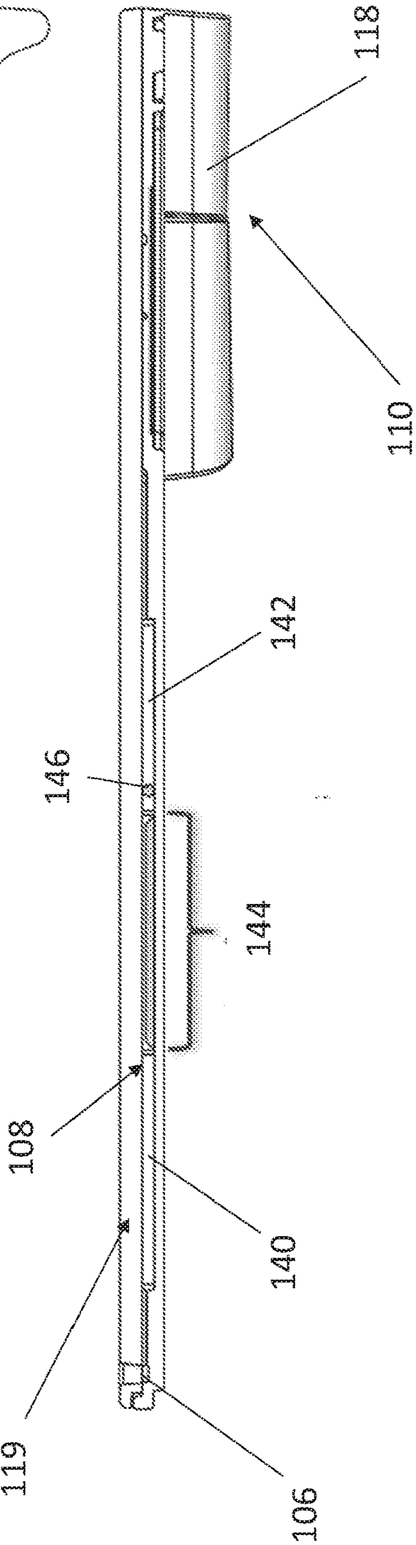

In embodiments, as shown in FIGS. 1C-1E, cartridge 100 includes housing 102, which is suitably prepared from three individual sections, e.g., a cover section 184, a base section 186 and a manifold section 188, each mechanically connected to each other to form cartridge 100. Utilizing three sections connected together allows for easier preparation of the various parts of cartridge 100, as well as assembly. For example, channels, microchannels, or tubes that make up conduit 108, fluid inlet port 106, as well as optical sample wells 104, can be pre-formed or pre-placed into base section 186, and then connected together with cover section 184 and manifold section 188 to form the finished cartridge 100.

Methods for mechanically connecting the sections of cartridge 100 include various adhesives or glues, laser welding, ultrasonic welding, mechanical screws, or self-fitting connectors, as well as bands or clips. In additional embodiments, the mechanical connection can be carried out by thermal fusion or thermal bonding between the two sections. In embodiments, the various sections (184, 186, 188) of housing 102 can be injection molded and then thermally bonded or fusion bonded to each other, thereby suitably enclosing conduit 108, optical sample wells 104 and fluid inlet port 106. In further embodiments, one or all of cover section 184, base section 186 and manifold section 188, of housing 102, can be prepared using an opaque plastic, which reduces unwanted light passing through the housing during measurements, reducing cross-talk.

In embodiments, as shown in FIGS. 1A-1E, provided herein is a cartridge 100 for determining the presence and/or amount of a microbial contaminant in a sample, the cartridge comprising, a housing 102 including a cover section 184, a base section 186 mechanically connected to the cover section 184, and a manifold section 188 mechanically connected to the base section 186.

FIGS. 1A-1B show views of cartridge 100 containing each of the sections in which cover section 184 is visible (FIG. 1A), and in which base section 186 and manifold section 188 are visible (FIG. 1B).

Cover section 184 suitably includes various cut-outs and connection points (see FIG. 1C) for connecting the various components, and is suitably constructed from a clear plastic or polymeric composition.

Figures 2A, 2B, 2C, 2D:
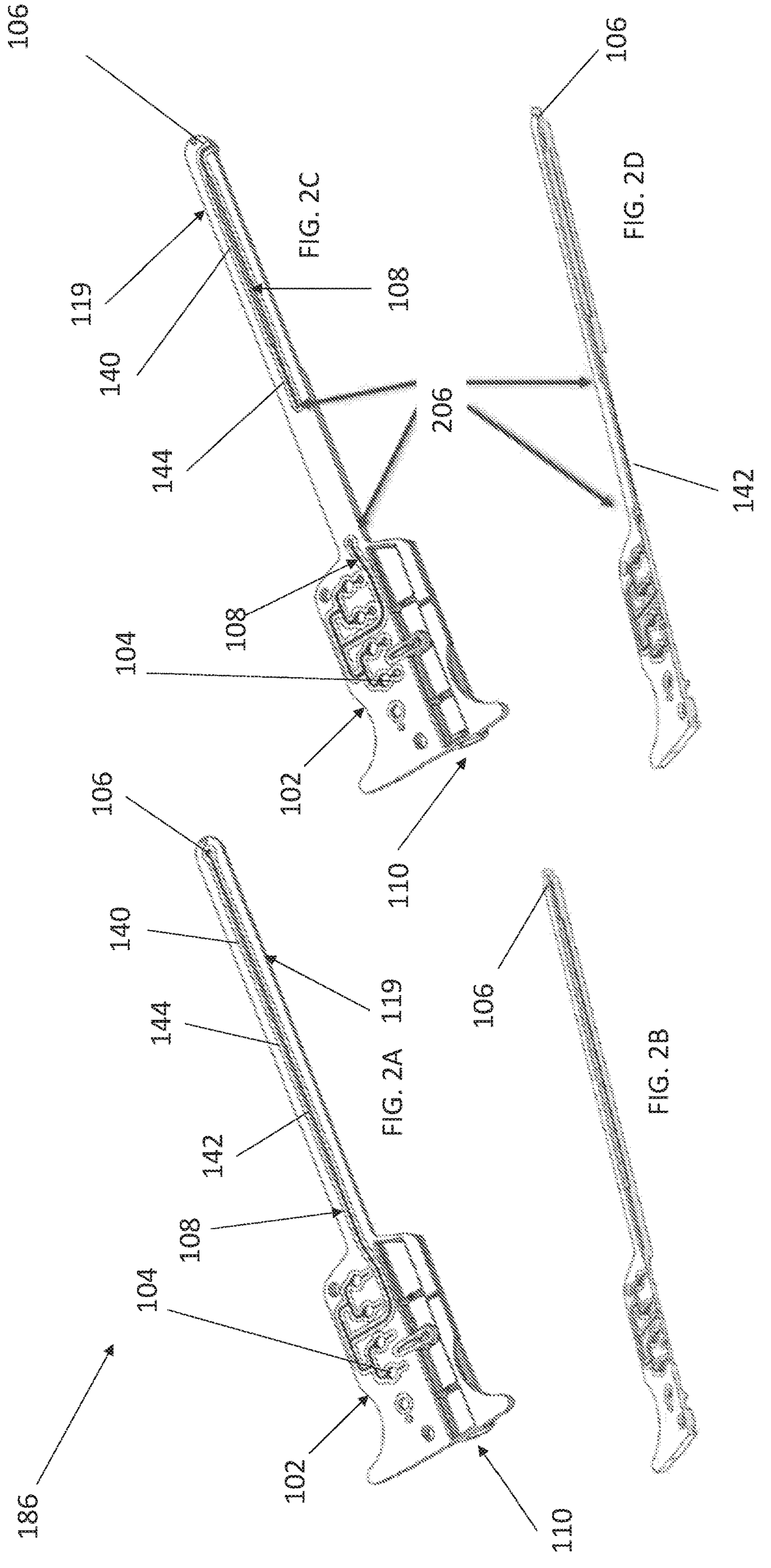
FIGS. 2A-2D show various views and components of cartridges for endotoxin detection in accordance with embodiments hereof.

Base section 186 is suitably a plastic element, that includes four optical sample wells 104, a fluid inlet port 106 and a conduit fluidly 108 connecting the fluid inlet port and the optical sample well. See FIG. 1F. Conduit 108 is suitably a cut-out or channel formed within the structure of base section 186, though in other embodiments can be a microfluidic channel or tubing that is added to the base section. FIGS. 1F-1G show one embodiment of a base section 186 in which conduit 108 runs continuously along one side of the base section 186, and contains within the conduit an aspiration zone 140, a fluid restrictor 144, and a mixing zone 142. This single planar embodiment of conduit 108 can be further seen in FIG. 1G in which all of the components of conduit 108 occur in the same plane. FIGS. 2A and 2B also show this planar embodiment, where conduit 108 runs the full length of the base section 186 from fluid inlet port 106 through to sample well 104. FIG. 2B shows a cross-section of the base section 186 taken through the conduit 108. Sample wells 104 shown in FIG. 2A are essentially the side-walls of the sample wells, with the top and bottom of the wells being provided by cover section 184 and manifold section 188, respectively. FIG. 2A shows exemplary locations of aspiration zone 140, fluid restrictor 144 and mixing zone 142, along the length of conduit 108.

In another embodiment, as illustrated in FIG. 1D, base section 186 can include a conduit 108 which begins on one side of the base section, then traverses through the base section 186 to the other side. For example, as illustrated in FIGS. 2C-2D, conduit begins on the "top" of the base section 186, connected to sample inlet port 106. Conduit 108 then traverses through base section 186 at first through hole 206, to the "under" side of base section 186, and back up at second through hole 206, to the "top" of the base section, prior to connecting to sample well 104. This "passing through" can also be seen in FIGS. 1A, 1B and 1D. FIG. 2C shows the position of aspiration zone 140 and fluid restrictor 144 on the "top" of base section 186. Mixing zone 142 can be seen below the base section 186, in the cross-section shown in FIG. 2D.

The manifold section 188 of cartridge 100 suitably includes a mixing portion 520 configured to include a dried composition comprising a hemocyte lysate, the mixing portion 520 corresponding to the mixing zone 142 of the conduit 108. That is that the mixing portion 520 of the manifold section 188 lines up with the mixing zone 142 of the conduit 108 in the base section 186 when the sections are connected to form the cartridge. In suitable embodiments, manifold section 188 also includes a sample well portion 504.

Figures 3A, 3B:
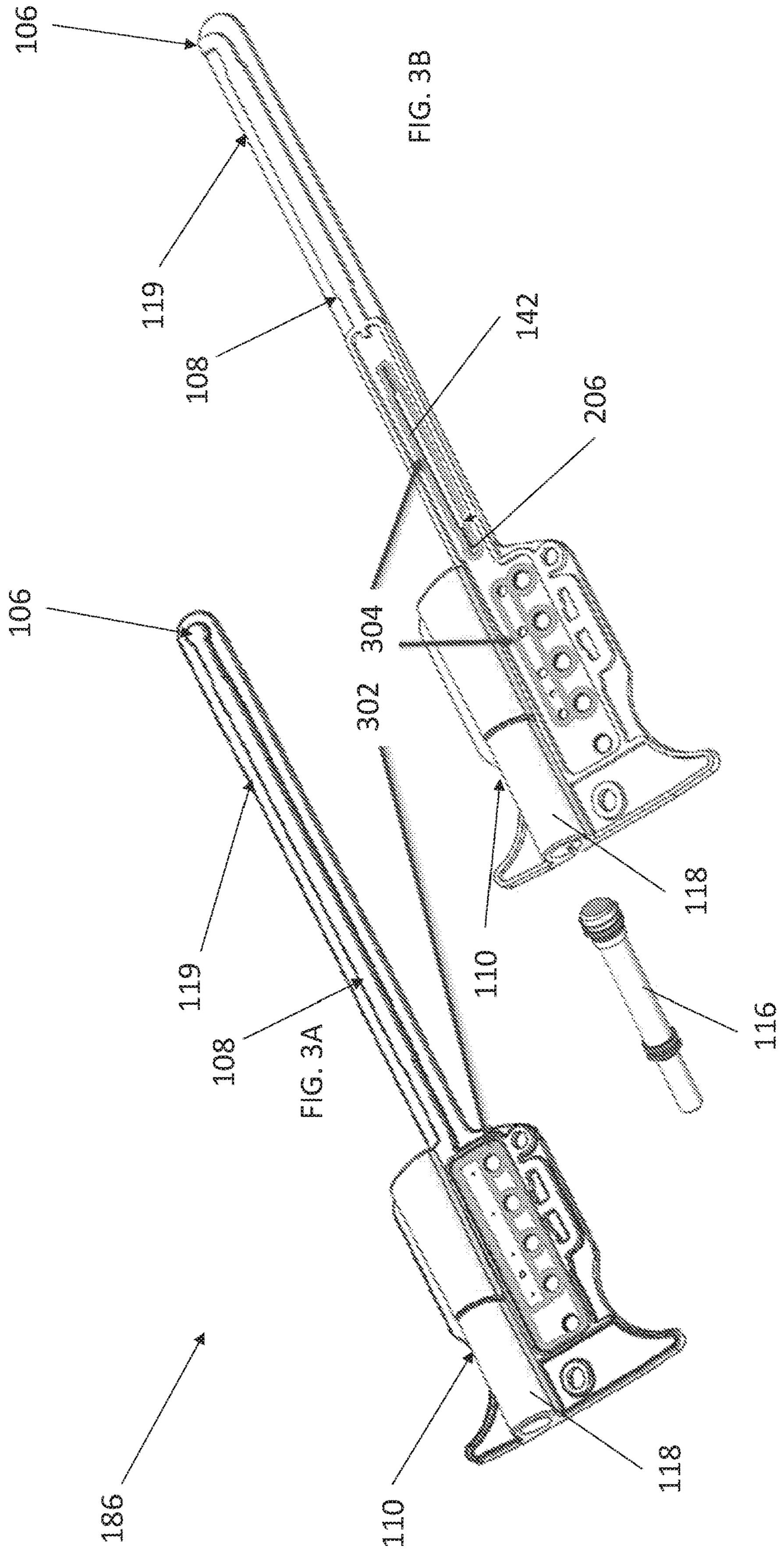
FIGS. 3A-3B show various views and components of base sections for use in a cartridge for endotoxin detection in accordance with embodiments hereof.
Figure 5A:
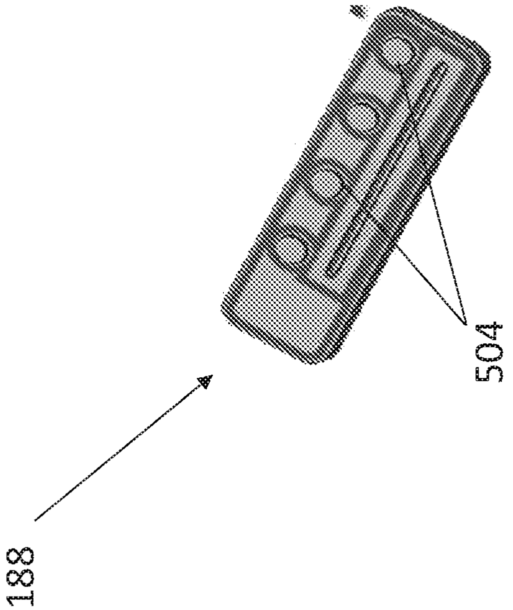
FIG. 5A shows a manifold section for use in a cartridge for endotoxin detection in accordance with embodiments hereof.
Figure 5C:
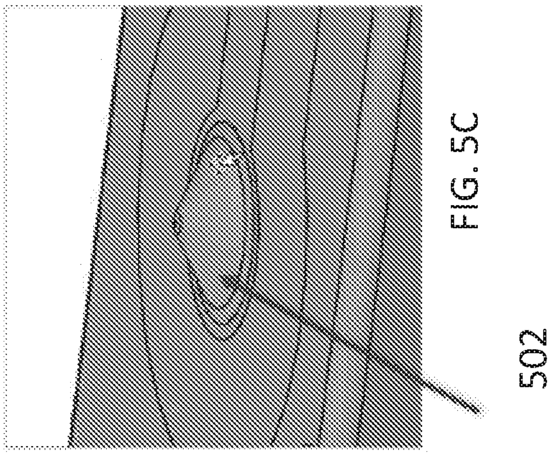
FIG. 5B-5C shows an additional manifold section for use in a cartridge for endotoxin detection in accordance with embodiments hereof.

FIG. 3A illustrates base section 186 in which conduit 108 is a single channel running the length of the long or slender section 119 of housing 102, from sample inlet port 106 to sample well 104, along one side of the base section 186. FIG. 3A shows a view of the base section 186 in which conduit 108 is a channel formed into the base section 186. FIG. 5A shows an embodiment of manifold section 188 which would fit into base section 186 at cut-out 302 of FIG. 3A. Manifold section 188 illustrated in FIG. 5A suitably includes sample well portions 504, which form the "bottom" of the sample wells 104, when connected together with cover section 184 and base section 186.

FIG. 3B illustrates another embodiment of base section 186 in which conduit 108 traverses through the base section via first and second through holes 206. As seen in FIG. 3B, conduit 108 begins as a channel formed into the base section 186, then crosses over via the first through hole 206. FIG. 3B illustrates cut-out 304 into which the manifold section 188 illustrated in FIG. 5B can be placed. The manifold section 188 in FIG. 5B suitably includes sample well portions 504, which form the "bottom" of the sample wells 104, when connected together with cover section 184 and base section 186, as well as mixing portion 520 that corresponds (i.e., matches up with) mixing zone 142 of base section 186 (see FIG. 1B, 1E, 2D and FIG. 3B). FIG. 1E also illustrates manifold 188 from FIG. 5B, prior to be connected to cover section 184 and base section 186, to form complete cartridge 100 (see also FIG. 1B, illustrating a view of the "bottom" of the cartridge where the manifold section 188 suitably fits).

Figure 4B:
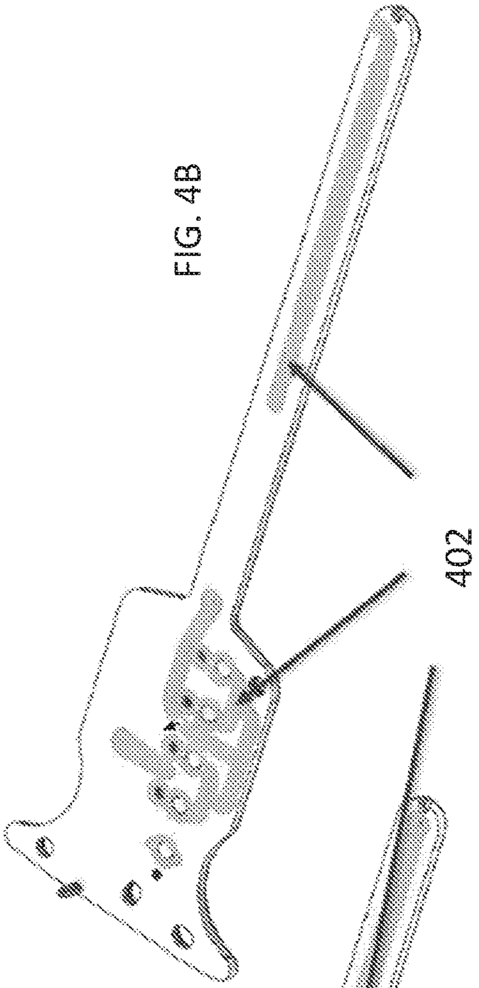
FIGS. 4A-4B show various views and components of cover sections for use in a cartridge for endotoxin detection in accordance with embodiments hereof.
Figure 4A:
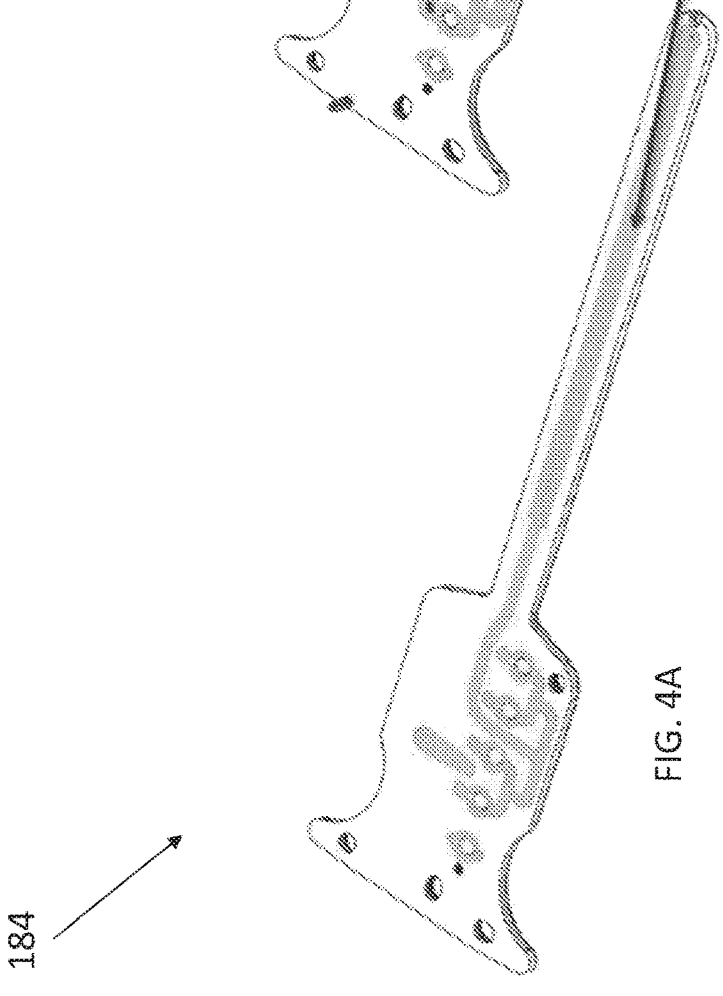
Figure 5B:
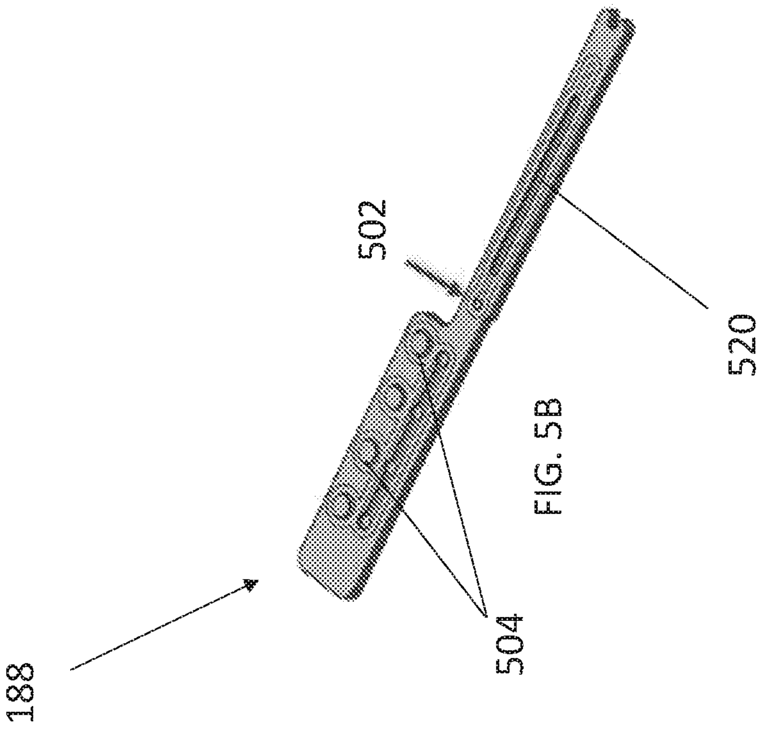

FIGS. 4A and 4B illustrate exemplary cover sections 184, with the cover section in FIG. 4A fitting with a single-channel conduit 108, and the cover section in FIG. 5B fitting with a conduit 108 that crosses over the base section. Exemplary areas where laser welding 402 can occur are shown.

As described herein, cartridge 100 suitably includes a pump mechanism 110 associated with the housing 102 and fluidly connected to the fluid inlet port 106, the conduit 108 and the (two) optical sample wells 104. With either design, pump mechanism 110 is suitably integrated into the base section 186 (i.e., made part of the base section 186), as shown in FIGS. 3A and 3B. In embodiments, the pump mechanism is a three-position syringe, wherein a first position creates a vacuum to introduce the sample into the aspiration zone 140, a second position provides transport from the aspiration zone 140, through the fluid restrictor 144, to the mixing zone 142, and a third position provides transport from the mixing zone 142 to the sample wells 104.

Suitably, as shown in exemplary embodiments and in the Figures, base section 186 includes four optical sample wells, wherein two of the four optical sample wells are configured to include an agent representative of the microbial contaminant dried in the optical sample wells. In embodiments, manifold section 188 suitably includes the agent representative of the microbial contaminant dried on a sample well portion 504 of the manifold section (FIG. 5A or 5B). In embodiments, the manifold section 188 further includes a chromogenic substrate dried on the mixing portion 520 of the manifold section 188, such that when the elements of the cartridge are connected, the manifold provides both of the components to the mixing zone 142. In suitable embodiments, the hemocyte lysate is limulus amoebocyte lysate and the agent in the sample wells is a bacterial endotoxin.

Thus, in embodiments, manifold section 188 is suitably prepared with all of the dried components useful in the assays described herein. Suitably, the sample well portions 504 of the manifold 188 include the agent representative of the microbial contaminant dried thereon, and the mixing portion 520 of the manifold section 188 includes both the hemocyte lysate and the chromogenic substrate that are provided to the mixing zone 142 dried thereon. The manifold section 188 can thus be a separately provided element of the cartridge, and one that can be removed and replaced, allowing for re-use of a cartridge if desired.

Manifold section 188 can also include a lens 502, that allows for the observation of the sample fluid coming into and/or out of the mixing zone 142. This lens 502 can be monitored optically by a laser or other light-based mechanism to confirm the position and location of the fluid sample during the analysis procedure.

Methods of Detection

Also provided herein are methods for detecting the presence of a microbial contaminant in a sample. In embodiments, the methods suitably include introducing the sample into the fluid inlet port of the cartridges described herein. For example, a sample can be held in a container, or can be pulled directly from a reaction process or batch, or a pharmaceutical solution. Suitably, the sample is introduced via sample introduction direction 114 by creating a vacuum via pump mechanism 110, suitably a three-position syringe, to introduce the sample into the fluid inlet port 106. The sample is also transferred to conduit 108 in this initial process, also suitably via the vacuum that is produced by pump mechanism. Suitably, the sample is transferred to the aspiration zone 140 of the conduit 108.

Then, pump mechanism 110, suitably a three-position syringe, is placed in second position and transfers the sample from conduit 108 (suitably the aspiration zone 140) to the mixing zone 142 of the conduit 108. In embodiments, this transferring occurs from the aspiration zone 140, through the fluid restrictor 144, and to the mixing zone 142.

The sample is then suitably mixed with the hemocyte lysate and the chromogenic substrate to generate a mixed sample. As described herein, this mixing suitably occurs via a magnetic mixing element 146, for example by spinning or translating the element within the mixing zone via a magnet. The mixed sample is then transferred from the mixing zone to the optical sample well 104. Suitably, the transferring or transporting of the sample is stopped by liquid impermeable membrane 121, which is fluidly connected to the optical sample well. As described herein, stopping the transporting allows each of the optical sample wells to fill substantially equally in volume (such that the volumes vary within about 10% of each other, suitably about 5%, or about 1%) to allow for comparison between the optical sample wells.

The methods further include measuring an optical property of the sample in the optical sample well. In the methods of detecting the presence of the microbial contaminant, a change in the optical property is indicative of the presence of the microbial contaminant in the sample.

As described herein, the optical property is suitably the absorbance of the sample at a preselected wavelength of light, and the change in the optical property is the change in absorbance. The optical property measured can be a change (e.g., an increase or decrease) in the absorbance at a particular wavelength, transmittance at a particular wavelength, fluorescence at a particular wavelength, or optical density. For example, the optical property may be a change in absorbance or transmittance at a wavelength in the range from about 200 nm to about 700 nm, and more suitably in the range from about 350 nm to about 450 nm, or about 400 nm to about 410 nm, or about 405 nm.

As described herein, an exemplary mechanism for sealing or connecting cover section 184, base section 186 and manifold section 188 of cartridge 100 includes laser welding and ultrasonic welding. Suitably, one or more of these sections is prepared from a polymeric material, such as polystyrene, which contains a small amount (e.g., 0.5-10%, suitably 2-5% by weight) of carbon black. Inclusion of carbon black one or more of the sections allows for the sections to be laser welded together. Methods for carrying out the laser welding are known in the art, for example as disclosed in Klien, "Laser Welding of Plastics," Wiley-VCH, Germany (2012), the disclosure of which is incorporated by reference herein in its entirety. Use of laser welding reduces concerns related to heat-caused degradation of the liquid impermeable membrane.

Methods of ultrasonic welding are well known in the art, for example as disclosed in Shoh, "Welding of thermoplastics by ultrasound," Ultrasonics 14: 209-217 (1976), the disclosure of which is incorporated by reference herein in its entirety. Use of ultrasonic welding reduces concerns related to heat-caused degradation of the liquid impermeable membrane.

Figure 6:
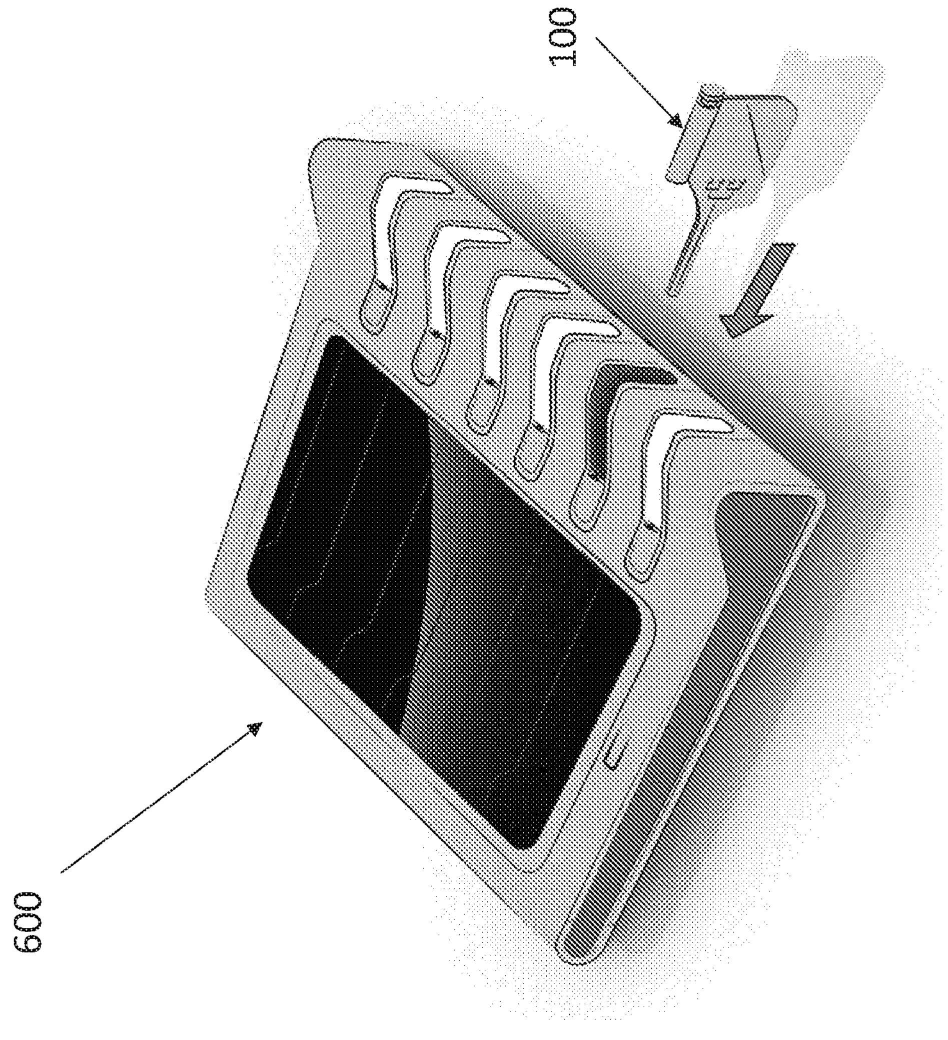
FIG. 6 shows an exemplary reader for use with cartridges described herein.

In exemplary embodiments, the cartridges 100 described herein, containing the sample in optical sample wells 104, can be inserted in a measurement device or reader device 600, such as shown in FIG. 6. It should be noted that reader device 600 in FIG. 6 is provided only for illustrative purposes, and does not limit the scope of the invention, including how the cartridges described herein are read or analyzed. Cartridge 100 is suitably inserted into reader device 600, such that the measurement of an optical property of the sample can take place. As shown, reader device 600 is suitably a hand-held or readily portable device that can be taken into various laboratory or clinical settings and easily manipulated and controlled via simple touch screen commands. Exemplary components of reader device 600 can include a light source, suitably an LED light source which is capable of producing light at a wavelength of about 350 nm to about 450 nm, or about 400 nm to about 410 nm, or about 405 nm. Also included in reader device 600 is a light panel (for example a light guide, mirror, prism, etc.), which provides illumination to each of optical sample wells 104, to provide signal channels, which can be read by a detector, suitably an array of photodiodes. A further reference channel is provided as a control to determine if the correct intensity and wavelength of light is being provided. A reader device 600 can also include a heater for example to maintain the temperature of a sample suitably to about 25° C. to about 40° C., to facilitate an enzymatic reaction. Exemplary heaters can be prepared from flexible films of polyimide, for example DUPONT KAPTON®, and silicone rubber. Various other components of reader device 600, such as computer circuitry for conducting the determination and/or quantification of the amount of absorbance are well known in the art and can be readily integrated into such devices.

Upon insertion of cartridge 100 into reader device 600, heating can occur via a heater to facilitate the desired enzymatic reaction. Light is provided through optical sample wells 104, which contain the sample, and the absorbance is read at a detector, suitably a photodiode. The absorbance from the various optical sample wells are then compared, with suitably one or more of the optical sample wells acting as a control which contains a microbial contaminant. The presence and/or amount of endotoxin in the sample can then be determined by comparing the amount in the sample, with that in the control, to a standard calibration curve, for example. An ordinarily skilled artisan can readily prepare such standard calibration curves using absorbance of known amounts of endotoxin. In additional embodiments, reader device 600 can also be provided with archived (i.e., maintained and initially provided on the reader device), or pre-determined standard curves, that can be used by an operator to determine the amount of endotoxin in a test sample. Such archived or pre-determined standard curves can be provided for various endotoxins and can be updated as needed by a user, for example by downloading standard curves from a maintenance database, etc. Multiple cartridges 100 can be inserted into reader device 600 and read at the same time, allowing for the presence and/or quantity of microbial contaminants in many different samples to be determined at the same time.

Additional Exemplary Embodiments

Embodiment is a cartridge for determining the presence and/or amount of a microbial contaminant in a sample, the cartridge comprising: a housing including an optical sample well, a fluid inlet port and a conduit fluidly connecting the fluid inlet port and the optical sample well; a pump mechanism associated with the housing and fluidly connected to the fluid inlet port, the conduit and the optical sample well; a mixing zone located along the conduit configured to include a dried composition including a hemocyte lysate.

Embodiment 2 includes the cartridge of embodiment 1, wherein the housing includes four optical sample wells, wherein two of the four optical sample wells are configured to include an agent representative of the microbial contaminant dried in the optical sample wells.

Embodiment 3 includes the cartridge of embodiment 1 or embodiment 2, further comprising a chromogenic substrate dried in the mixing zone.

Embodiment 4 includes the cartridge of any of embodiments 1-3, wherein the housing includes a cover section and a base section, mechanically connected to each other.

Embodiment 5 includes the cartridge of embodiment 4, wherein the housing further includes a manifold section mechanically connected to the base section, and wherein the dried composition is dried on a mixing portion of the manifold section.

Embodiment 6 includes the cartridge of embodiment 5, wherein the mixing portion further includes the chromogenic substrate dried thereon.

Embodiment 7 includes the cartridge of embodiment 5 or embodiment 6, wherein the manifold section further includes the agent representative of the microbial contaminant dried on a sample well portion of the manifold section.

Embodiment 8 includes the cartridge of any of embodiments 1-7, wherein the mixing zone includes a magnetic stirring element contained therein.

Embodiment 9 includes the cartridge of any of embodiments 1-8, wherein the conduit includes an aspiration zone and a fluid restrictor, located between the fluid inlet port and the mixing zone.

Embodiment 10 includes the cartridge of any of embodiments 1-9, wherein the hemocyte lysate is limulus amoebocyte lysate.

Embodiment 11 includes the cartridge of embodiment 2, wherein the agent representative of the microbial contaminant is a bacterial endotoxin.

Embodiment 12 includes the cartridge of any of embodiments 9-11, wherein the pump mechanism is a three-position syringe, wherein a first position creates a vacuum to introduce the sample into the aspiration zone, a second position provides transport from the aspiration zone, through the fluid restrictor, to the mixing zone, and a third position provides transport from the mixing zone to the sample well.

Embodiment 13 is a cartridge for determining the presence and/or amount of a microbial contaminant in a sample, the cartridge comprising: a housing including a cover section, a base section mechanically connected to the cover section, and a manifold section mechanically connected to the base section; the base section including two optical sample wells, a fluid inlet port and a conduit fluidly connecting the fluid inlet port and the optical sample well; the conduit including an aspiration zone, a fluid restrictor, and a mixing zone; the manifold section including a mixing portion configured to include a dried composition comprising a hemocyte lysate, the mixing portion corresponding to the mixing zone of the conduit; and a pump mechanism associated with the housing and fluidly connected to the fluid inlet port, the conduit and the two optical sample wells.

Embodiment 14 includes the cartridge of embodiment 13, wherein the base section includes four optical sample wells, wherein two of the four optical sample wells are configured to include an agent representative of the microbial contaminant dried in the optical sample wells.

Embodiment 15 includes the cartridge of embodiment 14, wherein the manifold section further includes the agent representative of the microbial contaminant dried on a sample well portion of the manifold section.

Embodiment 16 includes the cartridge of any of embodiments 13-15, further comprising a chromogenic substrate dried on the mixing portion of the manifold section.

Embodiment 17 includes the cartridge of any of embodiments 13-16, wherein the pump mechanism is integrated into the base section, and the pump mechanism is a three-position syringe, wherein a first position creates a vacuum to introduce the sample into the aspiration zone, a second position provides transport from the aspiration zone, through the fluid restrictor, to the mixing zone, and a third position provides transport from the mixing zone to the sample wells.

Embodiment 18 includes the cartridge of any of embodiments 13-17, wherein the hemocyte lysate is limulus amoebocyte lysate.

Embodiment 19 includes the cartridge of any of embodiments 14-18, wherein the agent is a bacterial endotoxin.

Embodiment 20 is a method for detecting the presence of a microbial contaminant in a sample, the method comprising: introducing the sample into the fluid inlet port of the cartridge of embodiment 3, and transferring the sample to the conduit; transferring the sample into the mixing zone of the conduit; mixing the sample with the hemocyte lysate and the chromogenic substrate to generate a mixed sample; transferring the mixed sample from the mixing zone to the sample well; and measuring an optical property of the mixed sample in the optical sample well, wherein a change in the optical property is indicative of the presence of the microbial contaminant in the sample.

Embodiment 21 includes the method of embodiment 20, wherein the measuring the optical property is a change in absorbance of light at a preselected wavelength.

Embodiment 22 includes the method of embodiment 21, wherein the change in absorbance of light at a preselected wavelength is compared to a standard curve.

Embodiment 23 includes the method of embodiment 22, wherein the standard curve is an archived standard curve.

Embodiment 24 includes the method of any of embodiments 20-23, wherein the introducing the sample comprises creating a vacuum via the pump mechanism to introduce the sample into the fluid inlet port and the conduit.

Embodiment 25 includes the method of any of embodiments 20-24, wherein the transferring comprises transporting via the pump mechanism the sample from mixing zone to the optical sample well.

Embodiment 26 is a method for detecting the presence of a microbial contaminant in a sample, the method comprising: introducing the sample into the fluid inlet port of the cartridge of embodiment 16, and transferring the sample to the aspiration zone; transferring the sample from the aspiration zone, through the fluid restrictor, to the mixing zone; mixing the sample with the hemocyte lysate and the chromogenic substrate to generate a mixed sample; transferring the mixed sample to the optical sample wells; and measuring an optical property of the mixed sample in the optical sample wells, wherein a change in the optical property is indicative of the presence of the microbial contaminant in the sample.

Embodiment 27 includes the method of embodiment 26, wherein the measuring the optical property is a change in absorbance of light at a preselected wavelength.

Embodiment 28 includes the method of embodiment 27, wherein the change in absorbance of light at a preselected wavelength is compared to a standard curve.

Embodiment 29 includes the method of embodiment 28, wherein the standard curve is an archived standard curve.

Embodiment 30 includes the method of any of embodiments 26-29, wherein the introducing the sample comprises creating a vacuum via the pump mechanism to introduce the sample into the fluid inlet port and the aspiration zone, the transferring in b) comprising transporting via the pump mechanism the sample from the aspiration zone to the mixing zone; and the transferring in d) comprises transporting via the pump mechanism the mixed sample from mixing zone to the optical sample wells.

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims or items are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

What is claimed is:

1. A cartridge for determining the presence and/or amount of a microbial contaminant in a sample, the cartridge comprising:

a. a housing including a cover section, a base section mechanically connected to the cover section, and a manifold section mechanically connected to the base section;

i. the base section including two optical sample wells, a fluid inlet port and a conduit fluidly connecting the fluid inlet port and the optical sample wells, wherein the base section includes side-walls of the optical sample wells;

ii. the conduit including an aspiration zone, a mixing zone, and a fluid restrictor comprising a structure or a narrowing of the conduit configured to reduce flow between the aspiration zone and the mixing zone so as to allow proper filling of the aspiration zone;

iii. the manifold section including a mixing portion including a dried composition comprising a hemocyte lysate, the mixing portion structurally matching up with the mixing zone of the conduit, and a sample well portion structurally matching up with the optical sample wells of the base section, wherein the manifold section is connected together with the cover section and the base section such that the sample well portion forms the bottom of the optical sample wells of the base section;

wherein the base section is positioned between the cover section and the manifold section; and b. a pump mechanism integrated into the base section; fluidly connected to the fluid inlet port, the conduit and the two optical sample wells; the pump mechanism comprising a three-position syringe, wherein a first position creates a vacuum to introduce the sample into the aspiration zone, a second position provides transport from the aspiration zone, through the fluid restrictor, to the mixing zone, and a third position provides transport from the mixing zone to the sample wells.

2. The cartridge of claim 1, wherein the base section includes four optical sample wells, wherein two of the four optical sample wells are configured to include an agent representative of the microbial contaminant dried in the optical sample wells.

3. The cartridge of claim 2, wherein the manifold section further includes the agent representative of the microbial contaminant dried on the sample well portion of the manifold section.

4. The cartridge of claim 1, further comprising a chromogenic substrate dried on the mixing portion of the manifold section.

5. The cartridge of claim 1, wherein the hemocyte lysate is limulus amoebocyte lysate.

6. The cartridge of claim 2, wherein the agent is a bacterial endotoxin.

* * * * *